US00PP37718P2

(12) United States Plant Patent
Moucheboeuf

(10) Patent No.: US PP37,718 P2
(45) Date of Patent: Sep. 29, 2026

(54) ***DIANTHUS* PLANT NAMED 'KLEDA28787'**

(50) Latin Name: ***Dianthus* x *allwoodii hort***
Varietal Denomination: KLEDA28787

(71) Applicant: KLEMM + SOHN GMBH & CO. KG, Stuttgart (DE)

(72) Inventor: Laetitia Moucheboeuf, Exeter (GB)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/359,504

(22) Filed: Oct. 15, 2025

(51) Int. Cl.
*A01H 5/02* (2018.01)
*A01H 6/30* (2018.01)

(52) U.S. Cl.
USPC ..... Plt./273
CPC ..... *A01H 6/30* (2018.05)

(58) Field of Classification Search
USPC ..... Plt./273
CPC ..... A01H 5/02
See application file for complete search history.

(56) References Cited

PUBLICATIONS https://www.gardencentermag.com/article/2025-new-perennial-varieties-guide/; Oct. 14, 2025; 2 pages.*
https://www.nurserymag.com/article/2025-new-perennial-varieties-guide/; Oct. 14, 2025; 2 pages.*
chrome-extension://efaidnbmnnnibpcajpcglclefindmkaj/https://media.planthaven.com/dev/docs/2025/04/Dianthus-SCENT-FIRST%C2%AE-Orange-Sparkler-PK.pdf; Apr. 2025; 1 page.*
https://www.youtube.com/watch?v=qT7Gky_7Z_o; Apr. 1, 2025; 1 page.*

* cited by examiner

*Primary Examiner* — Kent L Bell
(74) *Attorney, Agent, or Firm* — Weatherly IP Solutions, LLC; Karen P. Bechtold; James M. Weatherly

(57) ABSTRACT

A new *Dianthus* plant designated 'KLEDA28787' particularly distinguished by double flowers with an orange flower color with occasional pinkish flecks, a compact and mounding foliage habit, and tall, upright flowers; is disclosed.

1 Drawing Sheet

Genus and species: *Dianthus* x allwoodii hort.
Variety denomination: 'KLEDA28787'.

BACKGROUND OF THE NEW PLANT

The present invention comprises a new and distinct variety of *Dianthus,* botanically known as *Dianthus* x allwoodii hort. and hereinafter referred to by the variety name 'KLEDA28787'. 'KLEDA28787' originated from a branch mutation of 'WAS 19.01' (unpatented) discovered in July 2020 in a nursery in Ashcombe, Dawlish, United Kingdom.

In July 2020, 'KLEDA28787' was selected and was first vegetatively propagated by vegetative cuttings in Ashcombe, Dawlish, United Kingdom. KLEDA28787' was found to reproduce true to type in successive generations of asexual propagation in Ashcombe, Dawlish, United Kingdom via vegetative cuttings.

SUMMARY

The following are the most outstanding and distinguishing characteristics of 'KLEDA28787' when grown under normal horticultural practices in Dawlish, United Kingdom.

1. Double flowered habit, with orange flower color with occasional pinkish flecks; and
2. Compact and mounding foliage habit, and tall, upright flowers.

DESCRIPTION OF THE PHOTOGRAPH

This new *Dianthus* plant is illustrated by the accompanying photograph of a 9-month-old plant taken in June 2025 indoor in Dawlish Devon, United Kingdom. The colors shown are as true as can be reasonably obtained by conventional photographic procedures.

The photograph is a whole plant photo of 'KLEDA28787' and shows the foliage, buds, and flowers.

DESCRIPTION

The following detailed descriptions set forth the distinctive characteristics of 'KLEDA28787'. The data which define these characteristics were collected from 9-month-old plants in June 2025 indoors in Dawlish, United Kingdom. Color references are to The R.H.S. Colour Chart of The Royal Horticultural Society of London (R.H.S.), 6$^{th}$ edition (2015).

Classification:
- *Family*.—Caryophyllaceae.
- *Botanical*.—*Dianthus* x allwoodii hort.
- *Designation*.—'KLEDA28787'.
- *Type*.—Perennial carnation.

Parentage:
- *Mutation parent*.—'WAS.19.01' (unpatented).

Plant:
- *Propagation type*.—Vegetative via shoot cuttings.
- *Time to produce a rooted young plant*.—5 weeks to produce a rooted plug.
- *Root description*.—Fibrous, fine roots, RHS156D. Rooting habit shape: Fibrous. Plant form: Compact and mounding foliage habit, and tall, upright flowers.

Plant height: 28.0 cm to 33.0 cm. Plant diameter or spread: 20.0 cm to 23.0 cm.

Lateral branches/stems (shoot before elongation):

*Shape of the branch in cross-section*.—Circular.
*Hollowness of the branch*.—Absent.
*Length*.—14.0 cm to 16.0 cm.
*Diameter*.—0.5 cm.
*Internode length*.—0.5 cm.
*Internode quantity per shoot*.—7.
*Number of internodes per branch/stem*.—7.
*Node length*.—0.5 cm.
*Node diameter*.—0.5 cm.
*Texture*.—*Smooth*.
*Color* (*in sheathing zone*).—Between RHS 145B and RHS 145D.

Lateral branches/stems (flower stem):

*Shape of the branch in cross-section*.—Circular.
*Hollowness of the branch*.—Absent.
*Length*.—28.0 cm to 30.0 cm.
*Diameter*.—0.3 cm.
*Internode length*.—1.0 cm to 6.0 cm.
*Internode quantity per branch/stem*.—5 to 6 up to breaking point of the flower stem.
*Node length*.—0.3 cm to 0.4 cm.
*Node diameter*.—0.5 cm to 0.6 cm.
*Texture*.—Smooth.
*Color*.—RHS N189A.
*Flower clustering on the lateral branch*.—None.

Foliage:

*Arrangement*.—Opposite, sheathing and spiraling up the stem.
*Length*.—10.0 cm to 11.0 cm.
*Width*.—0.4 cm.
*Shape*.—Linear.
*Apex*.—Acute.
*Base*.—Decurrent.
*Margin*: Entire.
*Texture* (*both upper and lower surfaces*).—Smooth.
*Cross-section of the leaf*.—Flat to very weakly concave.
*Curvature of the leaf*.—Absent or very weakly concave.
*Glaucosity of the leaf*.—Medium to strong.
*Leaf color* (*both immature and mature*).—Immature: Upper surface: RHS 189B. Lower surface: RHS 189B. Mature: Upper surface: RHS 189A. Lower surface: RHS 189A.
*Venation pattern*.—Absent.

Flowers:

*Flower type and habit*.—Double, polypetalous.
*Fragrance*.—Present, medium to strong.
*Position of the flowers compared to the foliage of the plant*.—Far above.
*Profile of both the upper and lower part in the lateral view*.—Convex and concave.
*Diameter of the flower*.—5.0 cm to 5.5 cm.
*Natural flowering season*.—May to October.
*Number of flowers per spray*.—4 to 6.
*Flower longevity on the plant*.—10 to 20 days.

Buds (before cracking color):

*Length*.—2.0 cm.
*Diameter*.—1.3 cm.
*Shape*.—Obovate.
*Color*.—Upper part RHS 137D and 138A, lower part RHS 138B and 138D.
*Extrusion of the styles at the bud stage*.—Absent.

Corolla:

*Quantity of petals and arrangement*.—60 to 65 petals, persistent, apopetalous and overlapping.
*Corolla height*.—1.8 cm to 2.2 cm.
*Petal length*.—3.8 cm to 4.0 cm.
*Petal width*.—2.4 cm to 2.8 cm.
*Petal shape*.—Fan shaped.
*Petal apex*.—Obtuse.
*Petal base*.—Acute.
*Petal margin*.—Crenate-dentate.
*Depth of petal margin*.—Medium.
*Petal texture* (*both upper and lower surfaces*).—Smooth.
*Petal color*.—Immature: Upper surface: RHS 33D. Lower surface: RHS 29C. Mature: Upper surface: RHS 29C fading to RHS 159A. Lower surface: RHS 29D.
*Stripes/flecks*.—Present, few and occasional; color RHS 54B.
*Macule*.—N/A.

Calyx:

*Quantity of sepals and arrangement*.—Composed of 5 sepals, fused up to 1 cm below the apex.
*Longitudinal axis of the lobes of the calyx*.—Straight to angled.
*Shape*.—Funnel-shaped.
*Calyx height*.—2.2 cm to 2.4 cm.
*Calyx diameter* (*at the apex*).—1.7 cm to 2.0 cm.
*Calyx splitting*.—Observed occasionally.
*Sepal texture* (*both upper and lower surfaces*).—Smooth.
*Sepal color*.—Upper surface: RHS 138A at the apex and RHS 145A at the base. Lower surface: RHS 144D.
*Position of the outer lobes of the epicalyx in relation to the calyx*.—Adpressed.
*Apex shape of the outer lobes of the epicalyx*.—Acuminate.
*Tip length of the outer lobes of the epicalyx*.—Short.
*Position of the inner lobes of the epicalyx in relation to the calyx*.—Adpressed.
*Apex shape of the inner lobes of the epicalyx*.—Acuminate.
*Tip length of the inner lobes of the epicalyx*.—Short.

Peduncles:

*Length*.—28.0 cm to 30.0 cm.
*Diameter*.—0.3 cm.
*Strength*.—Strong.
*Texture*.—Smooth.
*Color*.—RHS N189A.

Reproductive organs:

*Stamens*.—Quantity per flower: 15 to 20. Filament length: 1.9 cm to 2.2 cm. Filament color: RHS NN155C. Anther length: 0.3 cm. Anther diameter: 0.2 cm. Anther color: RHS 160D (before dehiscence). Anther attachment and shape: Basifixed and sagittate. Pollen amount: Low.
*Pistil*.—Quantity per flower: 1 with 2 to 3 styles per flower. Length: 2.5 cm to 3.0 cm.
*Stigma*.—Color: RHS 69D. Shape: Linear and hairy along the style. Length: 0.5 cm to 0.7 cm. Diameter: 0.1 cm.
*Style*.—Color: RHS NN155B. Length: 1.5 to 2.0 cm. Diameter: 0.1 cm.

*Ovary*.—Size: 0.7 cm to 0.9 cm in length, 0.5 cm to 0.8 cm in diameter. Shape: Rhombic. Color: RHS 145B on the apical half and RHS 145D on the basal half.

Seeds: Not observed to date.

Disease and insect resistance: No particular disease or insect resistance observed to date.

COMPARISON OF 'KLEDA28787' WITH MUTATION PARENT AND KNOWN VARIETY

'KLEDA28787' is distinguished from the known mutation parent as described in Table 1.

TABLE 1

Comparison with Mutation Parent

| Trait or characteristic | 'KLEDA28787' | 'WAS.19.01' (unpatented) |
|---|---|---|
| Flower color and pattern | Orange with pinkish flecks | Yellow with pinkish flecks |

'KLEDA28787' can be compared to the commercial *Dianthus* variety 'WP10 SAB06' (U.S. Plant Pat. No. 24,363). Differences between the varieties are described in Table 2.

TABLE 2

Comparison with Similar Variety

| Trait or characteristic | 'KLEDA28787' | 'WP10 SAB06' (U.S. Plant Pat. No. 24,363) |
|---|---|---|
| Plant Height | Taller than 'WP10 SAB06' | Shorter than 'KLEDA28787' |
| Flower color and pattern | Orange with pinkish flecks | Coral |

I claim:

1. A new and distinct variety of *Dianthus* plant named 'KLEDA28787' as shown and described herein.

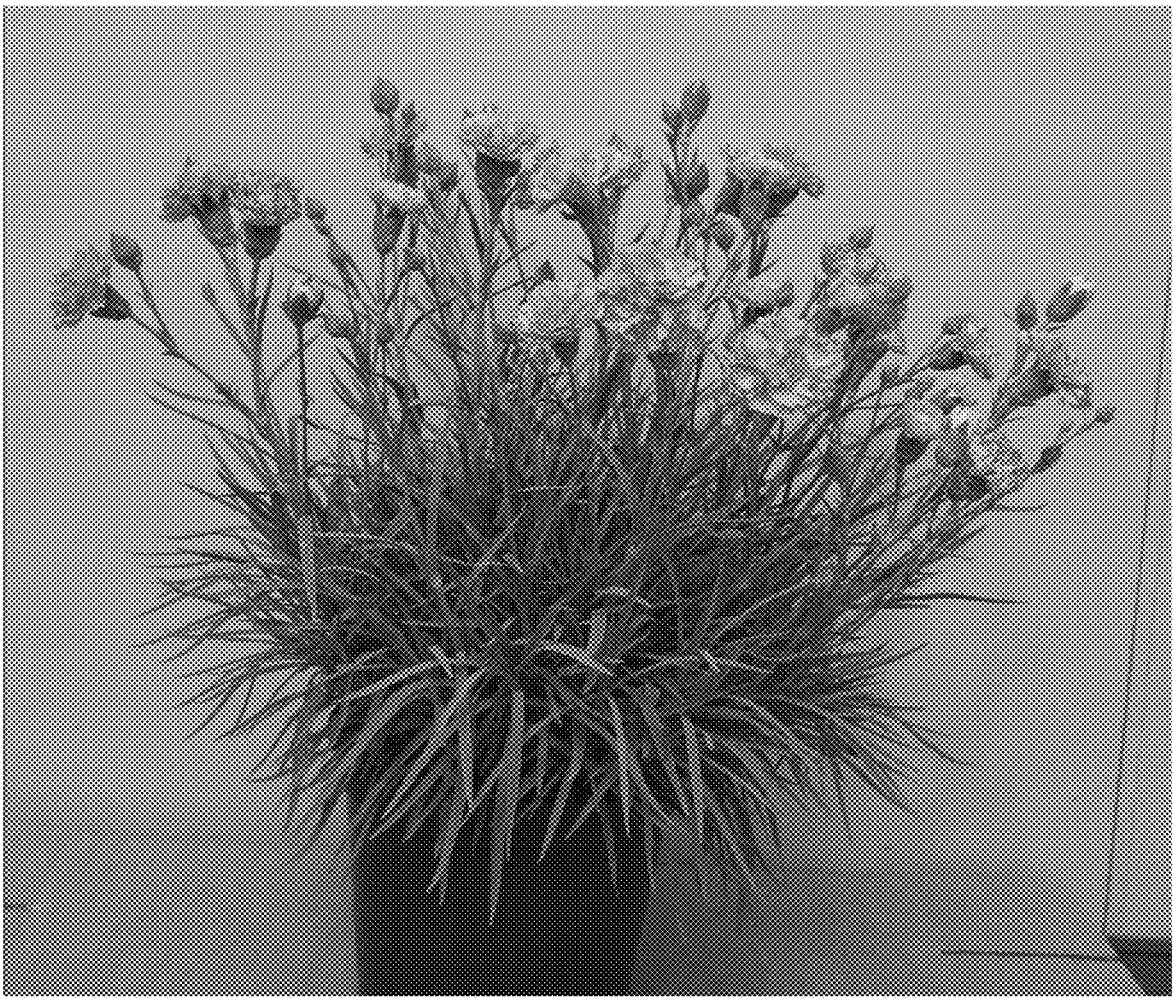

* * * * *